United States Patent [19]

Mechoulam et al.

[11] Patent Number: 5,605,928
[45] Date of Patent: Feb. 25, 1997

[54] ANTIEMETIC COMPOSITIONS

[75] Inventors: Raphael Mechoulam; Abraham Abrahamov, both of Jerusalem, Israel

[73] Assignee: Yissum Research Development Company of The Hebrew University in Jerusalem, Jerusalem, Israel

[21] Appl. No.: 343,604

[22] PCT Filed: May 27, 1993

[86] PCT No.: PCT/EP93/01335

§ 371 Date: Nov. 30, 1994

§ 102(e) Date: Nov. 30, 1994

[87] PCT Pub. No.: WO93/24125

PCT Pub. Date: Dec. 9, 1993

[30] Foreign Application Priority Data

Jun. 2, 1992 [IL] Israel ......................................... 102082

[51] Int. Cl.$^6$ ..................................................... A61K 31/35
[52] U.S. Cl. ............................................................. 514/454
[58] Field of Search .............................................. 514/454

*Primary Examiner*—Jerome D Goldberg
*Attorney, Agent, or Firm*—Keck, Mahin & Cate

[57] ABSTRACT

An antiemetic pharmaceutical composition for use in conjunction with oncological chemitherapy. The composition is of special value in pediatric oncological medicine. The active ingredient is Δ-8-tetrahydro-cannabinol, Δ-8-THC. Average unit dosage forms for use in pediatric medicine contain from about 4 mg/m$^2$ to about 20 mg/m$^2$ of the active compound.

6 Claims, No Drawings

ANTIEMETIC COMPOSITIONS

This application is a 371 of PCT/EP93/01335, filed May 27, 1993.

The present invention relates to antiemetic pharmaceutical compositions for use in human medicine, and more particularly in pediatric oncologic medicine. The drugs are of special value as antiemetic in pediatric oncology.

Cannabis has been used for millenia as antiemetic. After the identification of delta-9-tetrahydro-cannabinol (delta-9-THC), as the psychoactive constituent of cannabis, it was evaluated as anti-vomiting agent. It was found useful as antiemetic in the chemotherapy of cancer, and is marketed today commercially under the name of Dronabinol. It has a limited effectivity, and prevents vomiting and nausea in about 20 to 30 per cent of treated patients, and reduces such symptoms in another 40 to 50 per cent, having little or no effect in the rest. Pronounced side effects are drowsiness, dizziness and in some cases—anxiety. Such symptoms are pronounced with elderly patients, while younger ones undergo mainly mood changes.

J. Pharm. Sci., 1972, vol. 61, pages 1106 to 1112, describes the oral and parenteral use of marijuana constituents.

Int. J. Pharmaceutics, 1988, vol. 43, pages 9 to 15, describes the skin permeation behaviour of tetrahydrocannabinol through rat and human skin in vitro.

J. Natl. Cancer Inst., 1975, vol. 55, p. 597 to 602, is a general article dealing with anti-cancer therapy based on cannabinoids.

The invention relates to pharmaceutical antiemetic compositions for use as a highly effective antiemetic agent in children undergoing cancer therapy.

The compositions of the invention comprise as active ingredient an effective quantity of delta-8-THC, of the formula(I)

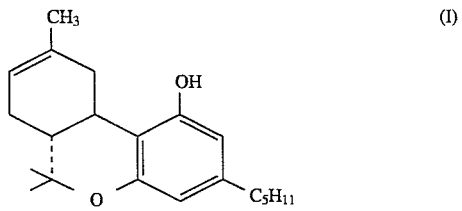

This compound is an isomer of delta-9-THC, and has been found to be at least as effective for the intended use as delta-9-THC, but has considerably reduced side-effects, especially in pediatric medicine. The compound delta-8-THC is considerably more stable towards various chemicals than the delta-9 isomer, and is less prone to oxidation. Furthermore, it can be produced easily and is less expensive than the delta-9-THC isomer.

There administration is per os, and various dosage forms were prepared.

The compositions of the invention were tried on patients, mainly children, before the administration of a variety of anti-cancer drugs. In all of these causes of nausea and vomiting, the compositions proved highly effective, and had negligible undesired side-effects. The experiments were carried out in the framework of an open label evaluation and results indicate that this composition is by far superior to existing ones.

The dosage administered is in the range of from about 5 mg to 20 mg, and preferably in the range of from 6 mg to about 15 mg. In oncology (pediatrics) the dosage is about 4 mg/m$^2$ to about 30 mg/m$^2$, and preferably about 10–18 mg/m$^2$ (surface area of the skin).

It was found that there can be administered to children doses which are larger than those which causes pronounced side-effects in adults. In pediatric use, essentially no side effects of significance were encountered. Doses of the order of 18 mg/m$^2$ did not cause undesired side-effects.

The effective component is generally administered in a vehicle such as an edible oil. Preferably the active compound is at least 80 per cent pure.

In a trial, with 8 children of 3 to 13 years age, with various blood cancers, treated with a variety of antineoplastic drugs, 18 mg/m$^2$, in edible oil, p.o. of delta-8-THC was given two hours before the antineoplastic drug, and repeated every 6 hours of 24 hours. Vomiting was completely prevented, with negligible side effects. So far these children have received $\Delta^8$-THC nearly 500 times (see Table).

PATIENTS AND METHODS

Eight children with various blood cancers were administered delta-8-THC at a dose of 18 mg/m$^2$ p.o. two hours before the start of the anticancer treatment. The drug was dissolved in corn or olive oil (6 mg/ml). The same dose was repeated every 6 hrs for 24 hrs. The treatment for each child is presented in the Table. Whenever additional cycles of antineoplastic therapy were required, delta-8-THC was administered following the same time procedure described above. Children received delta-8-THC only during days when emetogenic drugs were administered.

Established anticancer drug protocols were followed with all patients.

A study on vomiting due to antineoplastic therapy was carried out with 8 patients. Details of their antineoplastic treatment and side effects of the antiemetic therapy are presented in the Table. Chemotherapy protocols of the types indicated in the Table almost invariable cause intense vomiting, which starts about 2 hrs after the initiation of chemotherapy and gradually ends over a 24 hr period. In preliminary trials we tried to end the antiemetic therapy after the first or second dose of the cannabinoid, i.e. after 6 or 12 hrs. Vomiting started in most cases. Hence, in the recorded trial, all children were given 4 doses over 24 hrs. When antiemetic protocol described above was strictly followed no emesis was noted. In one case (patient D.E.) delta-8-THC therapy initially was refused. The patient experienced debilitating vomiting for 24 hrs after the antineoplastic treatment. During the second treatment cycle (which took place after 8 days), at the patient's family request, delta-8-THC treatment was initiated. No vomiting occurred.

As indicated in the Table the side effects observed with delta-8-THC were minor: some irritability as slight euphoria. No anxiety or hallucinogenic effects were noted in spite of the high doses administered.

The LD$_{50}$ values for Fischer rats treated orally with single doses of delta-9-THC and delta-8-THC, and observed for 7 days, are 1910 mg/kg and 1980 mg/kg (for males) respectively and 860 mg/kg (for females). The histopathological changes caused by these extremely high doses were essentially the same for both delta-8- and delta-9-THC. LD$_{50}$ could not be determined in either rhesus monkeys or dogs as single oral doses of up to 9000 mg/kg of either delta-8- or delta-9-THC in dogs or monkeys were non lethal. Histopathological alterations did not occur in either dogs or monkeys.

We found that infants and young children with different blood cancers, who were treated with a variety of anticancer drugs protocols could be administered doses of delta-8-THC considerably higher than the doses of delta-9-THC generally administered to adult cancer patients without the occurrence of major side effects (5–10 mg/m$^2$ of delta-9-THC generally recommended for adult patients versus 18 mg/m$^2$ of delta-8-THC used by us in children). Our antiemetic protocol for cancer patients, to which we strictly adhere, consists of one dose of delta-8-THC (18 mg/m$^2$) 2 hours before chemotherapy, followed by the same dose every 6 hours for a total of 4 doses per day. As mentioned above, the prevention of vomiting was complete regardless of the antineoplastic protocol followed.

TABLE

Delta-8-THC Administered to Children Treated for Various Blood Cancers.[a]

| No. | Name | Age, (years), sex | Diagnosis | Antineoplastic treatment | Number and Effect of antiemetic treatments |
|---|---|---|---|---|---|
| 1.* | A. M. | 10 m | A.L.L.[b] pre B, in relapse | Cytarabine-L-Asparaginase[c] | (32), no side effects |
| 2. | C. O. | 3.5 m | Hodgkin's disease | MOPP-ABV protocol[d] | (64), slight irritability during first 2 cycles |
| 3. | L. H. | 4 f | A.L.L., T type | BFM protocol[e] | (76), slight irritability and euphoria |
| 4. | M. H. | 3 f | Wilm's tumor, stage III | NWTS-4 protocol[f] | (30), no side effects |
| 5. | R. M. | 13 f | A.L.L. T type in second relapse | Cytarabine, Amsacrine protocol[g] | (24), no side effects |
| 6.** | D. E. | 7 m | Burkitt's lymphoma | Burkitt's lymphoma protocol[h] | (114), no side effects |
| 7.*** | K. K. | 6 f | A.L.L. | Rez BFM 87 protocol[i] | (64), no side effects |
| 8. | A. A. | 5 m | A.L.L. | BFM protocol[e] | (76), no side effects |

*Metoclopromide (0.3 mg/kg) p.o. or i.v. in previous treatment failed to prevent vomitting
**During first cycle, refusal to take THC caused profuse vomiting
***Treatment during remission after 2nd relapse and during 3rd relapse.
Footnotes to Table
[a] $\Delta$ — THC, 18 mg/m$^2$
[b] A.L.L. — acute lymphoblastic anemia
[c] Cytarabine and asparaginase
[d] Includes vincristine, procarbazine, doxorubicin, bleomycin, vinblastine
[e] Includes vincristine, daunorubicine, asparaginase, cyclophosphamaide, cytarabine, 6-meracaptopurine etoposide, methotrexate
[f] Includes vincristine, doxorubicin, dactinomycin
[g] Cytarabine and amsacrine
[h] Includes vincristine, doxorubicin, cyclophosphamide, methotrexate
[i] Includes 6-mercaptopurine, vincristine, methotrexate, cytarabine, teniposide, asparaginase

We claim:

1. A method for treating emesis in children undergoing anticancer chemotherapy which comprises orally administering to said children an effective amount of the compound of formula 1

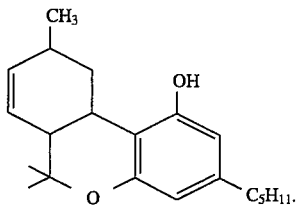
(I)

2. A method according to claim 1, in a form suitable for oral administration.

3. A method according to claim 2, wherein the active compound is administered with an edible oil.

4. A method according to claim 1, wherein the quantity comprises from 2 to 20 mg as total quantity of the compound of formula (I).

5. A method according to claim 4, wherein the dosage is between 3 to 15 mg as total quantity of the active compound.

6. A method according to claim 1, wherein the active compound is at least 80 per cent pure.

* * * * *